United States Patent [19]

Briner

[11] Patent Number: 5,006,552
[45] Date of Patent: Apr. 9, 1991

[54] CYCLOPENTANE DERIVATIVES

[75] Inventor: Paul H. Briner, Canterbury, England

[73] Assignee: Shell Internationale Research Maatschappij B.V., Netherlands

[21] Appl. No.: 397,288

[22] Filed: Aug. 23, 1989

[30] Foreign Application Priority Data

Aug. 31, 1988 [GB] United Kingdom ............ 8820603

[51] Int. Cl.$^5$ .................. A61K 31/335; C07D 303/40
[52] U.S. Cl. ..................................... 514/475; 549/546
[58] Field of Search ........................ 549/546; 514/475

[56] References Cited

U.S. PATENT DOCUMENTS 4,174,344 11/1979 Grethe et al. ................... 549/546

Primary Examiner—Richard L. Raymond
Assistant Examiner—Mark W. Russell

[57] ABSTRACT

The invention provides cyclopentane derivatives of the general formula

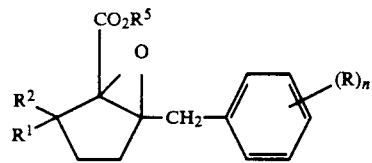

in which n represents an integer from 0 to 5, each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group, $R^1$ and $R^2$ independently represent a hydrogen atom or an alkyl group, and $R^5$ represents a hydrogen atom or an alkyl or cycloalkyl group; a process for their preparation; compositions containing such compounds and their use as fungicides. Compounds of formula I are also useful as intermediates in the preparation of certain fungicidally active cyclopentane derivatives.

9 Claims, No Drawings

CYCLOPENTANE DERIVATIVES

This invention relates to certain cyclopentane derivatives, a process for their preparation, compositions containing such compounds and their use as fungicides.

According to the present invention there is provided a compound of the general formula

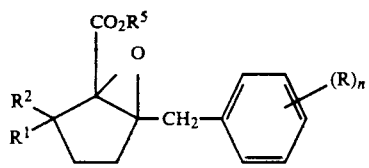
(I)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and $R^5$ represents a hydrogen atom or an alkyl or cycloalkyl group.

When any of the foregoing substituents represents or contains an alkyl substituent group, this may be linear or branched and may contain up to 12, preferably up to 6, and especially up to 4 carbon atoms. A cycloalkyl substituent group may contain 3 to 8, preferably 3 to 6, carbon atoms.

It is preferred that $R^1$ and $R^2$ independently represent a hydrogen atom or a $C_{1-4}$alkyl, particularly a methyl, group.

Preferably, R represents a halogen, especially a chlorine, atom.

It is also preferred that $R^5$ represents a hydrogen atom or a $C_{1-6}$alkyl group.

A particularly preferred sub-group of compounds of formula I is that in which n is 1, R represents a chlorine atom, preferably substituted at the 4-position of the phenyl ring, $R^1$ and $R^2$ both represent a hydrogen atom or both represent a methyl group; and $R^5$ represents a methyl group.

The present invention also provides a process for the preparation of a compound of formula I as defined above which comprises reacting a compound of the general formula

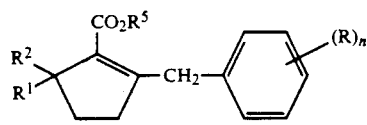
(II)

in which n, R, $R^1$, $R^2$ and $R^5$ are as defined above, with a peracid.

Up to 3, preferably 1 to 3, equivalents of peracid may be used. Preferably, the peracid is peracetic acid, perbenzoic acid or perphthalic acid. In the case of peracetic acid, this may be generated in situ, if desired, by reacting hydrogen peroxide with acetic acid.

The process may be carried out in the presence of a solvent. Suitable solvents include chlorinated solvents, such as dichloromethane and trichloromethane, esters and aromatic hydrocarbons.

The reaction is conveniently carried out at a temperature, from room temperature to the reflux temperature of the solvent, if used. The preferred temperature is from 30°–70° C.

Compounds of formula II may be conveniently prepared by heating a compound of the general formula

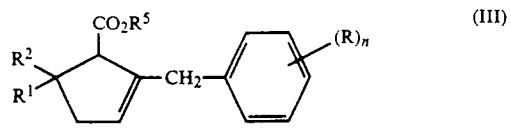
(III)

or the general formula

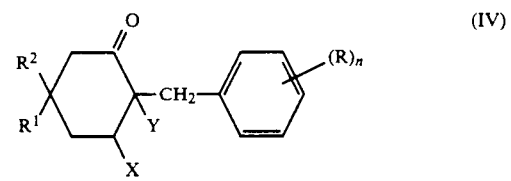
(IV)

in which n, R, $R^1$, $R^2$ and $R^5$ are as defined above and X and Y independently represent a halogen, preferably a chlorine or bromine, atom, with a compound of the general formula

$MOR^5$ (V)

in which $R^5$ is as defined above and M represents an alkali metal, preferably a sodium, atom, in the presence of a polar solvent. It is preferred that the polar solvent is a compound of the general formula

$R^5OH$ (VI)

in which $R^5$ is as defined above. Preferably, $R^5$ has the same meaning in formula V and formula VI. For instance, if the compound of formula V is sodium methoxide, it is preferred that the solvent of formula V is methanol. The compounds of formula II and a process for their preparation form the subject of copending patent application T 616.

Compounds of formula III may be conveniently prepared by reacting a compound of formula IV, as defined above, with a compound of formula V, as defined above, in the presence of a solvent VI, as defined above, preferably at a temperature in the range of 0°–20° C. The compounds of formula III and a process for their preparation form the subject of copending patent application T 616.

Compounds of formula IV may be conveniently prepared by reacting a compound of the general formula

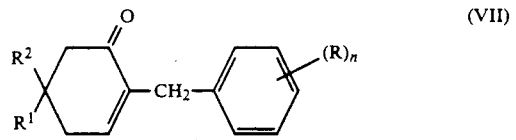
(VII)

in which n, R, $R^1$ and $R^2$ are as defined above, with a compound XY, in which X and Y are as defined above. Alternatively, compounds of formula IV may be generated in situ and then heated with a compound of formula V in the presence of a solvent of formula VI as described above to form compounds of formula II in a one-pot synthesis. The compounds of formula IV and a process for their preparation form the subject of copending patent application T 616.

Compounds of formula VII may be conveniently prepared by reacting a compound of the general formula

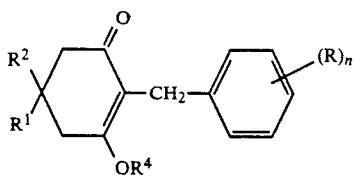

(VIII)

in which n, R, $R^1$ and $R^2$ are as defined above and $R^4$ represents an alkyl, preferably a $C_{1-4}$alkyl, group, with a suitable reducing agent, for instance, a complex metal hydride, such as lithium aluminium hydride or sodium aluminium hydride, or hydrogen in combination with a catalyst, and subsequently hydrolysing the reaction mixture. The compounds of formula VII and a process for their preparation form the subject of copending patent application T 616.

Compounds of formula VIII may be conveniently prepared by reacting a compound of the general formula

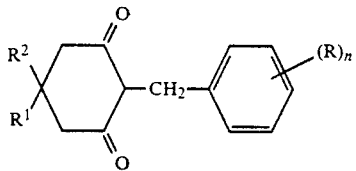

(IX)

in which n, R, $R^1$ and $R^2$ are as defined above, with a compound of the general formula $$R^4OH \qquad (X)$$

in which $R^4$ is as defined above, in the presence of an acid, such as sulphuric acid, p-toluenesulphonic acid or an ion exchange resin. The compounds of formula VIII and a process for their preparation form the subject of copending patent application T 616.

Compounds of formula IX may be conveniently prepared by reacting a compound of the general formula

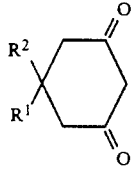

(XI)

in which $R^1$ and $R^2$ are as defined above, with a compound of the general formula

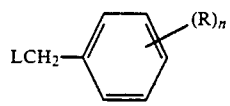

(XII)

in which R and n are as defined above and L represents a suitable leaving group, in the presence of a suitable base, such as potassium hydroxide.

Compounds of formula V, VI, X, XI and XII and the compounds XY are known compounds or can be prepared by processes analogous to known processes.

Certain compounds of the invention have exhibited useful fungicidal activity in specific screens. Thus, in accordance with another aspect of the invention there is provided a fungicidal composition which comprises a carrier and, as active ingredient, a compound of formula I as defined above. A method of making such a composition is also provided which comprises bringing a compound of formula I into association with at least one carrier. Such a composition may contain a single compound or a mixture of several compounds of the present invention.

A composition according to the invention preferably contains from 0.5 to 94% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the, molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a plant, or could include an adhesive component enabling them to be applied directly to the stem of a plant.

The invention still further provides the use as a fungicide of a compound of the general formula I as defined above, or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The compounds of formula I are also useful as intermediates in the preparation of fungicidally active cyclopentane derivatives of the general formula

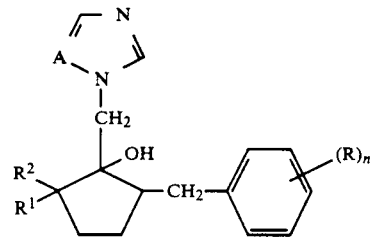

(XIII)

in which n, R, $R^1$ and $R^2$ are as defined above and A represents a nitrogen atom or a CH group. Certain compounds of formula XIII are the subject of co-pending patent applications GB-A1-2180236 and EP-A2-0267778.

The compounds disclosed in EP-A2-0267778 and GB-A1-2180236 exist in two stereoisomeric forms which have the following structures:

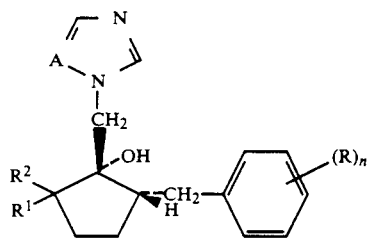

(XIIIA)

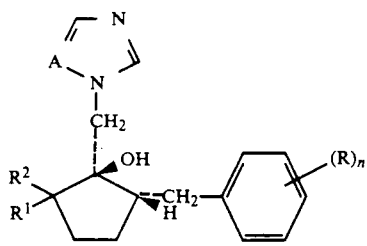

(XIIIB)

The letters A and B will be used hereinafter to denote compounds having the same stereochemical configuration as isomers A and B above.

Isomers A and B can be separated by, for instance, chromatography and exhibit different fungicidal activity. Generally, isomers of formula XIIIA exhibit greater fungicidal activity than isomers of formula XIIIB. The compounds of formula I exist as single stereoisomers having the following structure:

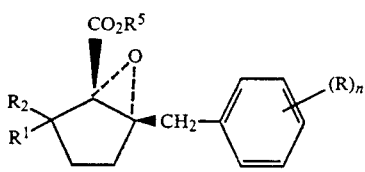

The process used to synthesise compounds of formula XIIIA from compounds of formula I is set out in the following reaction scheme:

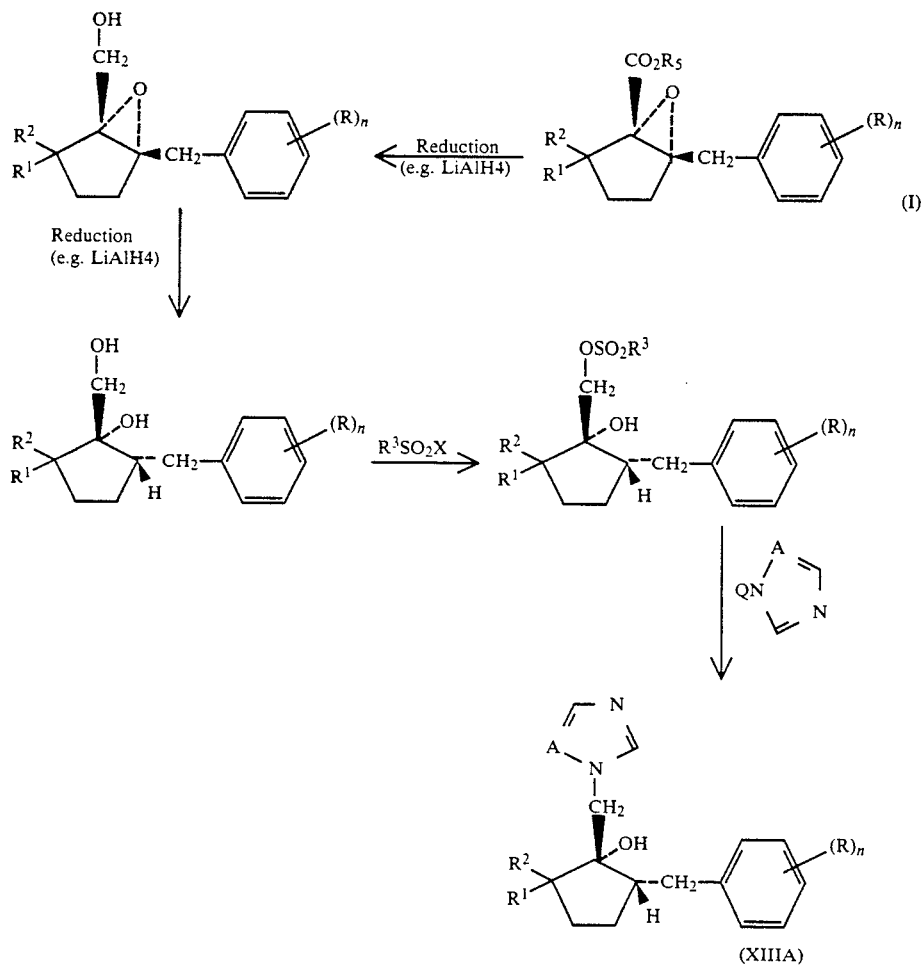

In the above reaction scheme, n, R, $R^1$, $R^2$, $R^5$, X and A are as previously defined, $R^3$ represents an optionally substituted alkyl or aryl group, preferably a $C_{1-4}$alkyl or a phenyl group each optionally substituted by one or more substituents selected from, halogen atoms, nitro, cyano, hydroxyl, $C_{1-4}$alkyl, $C_{1-4}$haloalkyl, $C_{1-4}$alkoxy, amino, $C_{1-4}$alkylamino, di-$C_{1-4}$alkylamino, $C_{1-4}$alkoxycarbonyl, carboxyl, $C_{1-4}$alkanoyl, $C_{1-4}$alkylthio, $C_{1-4}$alkylsulphinyl, $C_{1-4}$alkylsulphonyl, carbamoyl, $C_{1-4}$alkylamido, $C_{3-8}$cycloalkyl and phenyl groups, and Q represents a hydrogen or alkali metal, preferably sodium, atom. The intermediate compounds and process steps in the above reaction scheme are the subject of copending patent applications T 623 and T 626.

The invention is further illustrated by the following Examples

Example 1

Preparation of 1-(4-chlorobenzyl)-1,2-epoxy-3,3-dimethyl-2-methoxycarbonylcyclopentane (n=1, R=4-Cl, $R^1=R^2=CH_3$, $R^5=CH_3$)

(a) Preparation of 2-4-chlorobenzyl)-5,5-dimethylcyclohexane-1,3-dione 449 g (3.21 mols) dimedone (5,5-dimethylcyclohexane-1,3-dione) were added to a solution of aqueous potassium hydroxide comprising 166 g of 85% potassium hydroxide (2.52 moles) in 700 ml of water. The mixture was then warmed and a clear orange solution was obtained at 47° C. The solution was then heated to 59° C. and 544 g (3.21 mols) molten 4-chlorobenzyl chloride were added over a period of 1 hour with further heating to 85° C. Heating was continued for a further 2½ to 3 hours up to a temperature of 100° C. The mixture was then cooled, the solid product filtered off, washed with water and dried in a vacuum oven at 50° C. The crude solid (815 g) was then dissolved in 2400 ml methanol at reflux and 200 ml water added to produce a permanent cloudiness. The mixture was then allowed to cool to room temperature overnight with stirring The solid so obtained was filtered, washed with about 400 ml cold methanol and dried in a vacuum oven to produce 340 g 2-(4-chlorobenzyl)-5,5-dimethylcyclohexane-1,3-dione as a white solid, m.pt. 188–190° C. Yield: 42%.

(b) Preparation of 2-(4-chlorobenzyl)-3-(2-methylpropoxy)-5,5-dimethylcyclohex-2-en-1-one 325 g (1.23 mol) of the 2-(4-chlorobenzyl)-5,5-dimethylcyclohexane-1,3-dione obtained in (a), 1.6 litres toluene, 182 g (2.5 mol) isobutanol and 5 g p-toluenesulphonic acid were stirred together at reflux under a Dean-Stark apparatus. The temperature of the reaction mixture was approximately 90° C. As water distilled off, the reaction mixture changed from a thin slurry to a yellow solution. After 14 hours reflux, the reaction mixture was cooled and shaken twice with 500 ml aliquots of 10% aqueous sodium hydroxide. The toluene layer was then flashed to give 389 g yellow/orange oil which crystallised on standing. Recrystallisation of the solid from 60/80 petroleum produced 331 g 2-(4-chlorobenzyl)-3-(2-methylpropoxy)-5,5-dimethylcyclohex-2-en-1-one as a white crystalline solid, m.pt. 60-61° C. Yield: 84%.

(c) Preparation of 2-(4-chlorobenzyl)-3-methoxy-5,5-dimethylcyclohex-2-en-1-one

A solution of 154 g of the 2-(4-chlorobenzyl)-3-(2-methylpropoxy)-5,5-dimethylcyclohex-2-en-1-one obtained in Example 1 in 1200 ml methanol containing 3 g p-toluenesulphonic acid was refluxed for 2 hours. The reaction mixture was then extracted with 3 litres water and 1 litre diethyl ether and re-extracted with a further 1 litre diethyl ether. The organic phases were then back-washed first with 200 ml 10% aqueous sodium hydroxide and then with 100 ml saturated sodium chloride solution, dried over anhydrous magnesium sulphate and flashed. The residue was then crystallised in 60/80 petroleum, filtered and air-dried to give 98 g 2-(4-chlorobenzyl)-3-methoxy-5,5-dimethylcyclohex-2-en-1-one as a white solid, m.pt. 62-63° C. Yield: 73%.

(d) Preparation of 2-(4-chlorobenzyl)-5,5-dimethylcyclohex-2-en-1-one 98 g (0.35 mol) of the 2-(4-chlorobenzyl)-3-methoxy-5,5-dimethylcyclohex-2-en-1-one obtained in (c) were added to a slurry of 6.65 g (0.175 mol) lithium aluminium hydride in 490 mls diethyl ether at a rate sufficient to maintain reflux and the final reaction mixture refluxed for a further 30 minutes. 5 ml water were then added, followed by 5 ml 15% aqueous sodium hydroxide and a further 15 ml water and the resulting precipitate was filtered off. The filtrate was then shaken in 200 ml 5 M hydrochloric acid for five minutes and the organic layer then separated, washed twice with 100 ml aliquots of saturated sodium bicarbonate solution, dried over anhydrous magnesium sulphate and stripped. The resulting oil was then dissolved in 430 mls dichloromethane, 18 g (0.085 mols) pyridinium chlorochromate were added and the reaction mixture stirred for 3 hours. 600 ml diethyl ether were added and the solid was then filtered off. The filtrate was washed three times with 10% sodium hydroxide, once with 2.5 M hydrochloric acid and once with saturated sodium bicarbonate solution. It was then dried over anhydrous magnesium sulphate and stripped to give 82 g of crude product. Distillation of the crude product under reduced pressure (0.15 mm mercury) gave 79 g 2-(4-chlorobenzyl)-5,5-dimethylcyclohex-2-en-1-one, b.pt. 130° C. at 0.15 mm mercury. Yield: 91%.

(e) Preparation of 2-(4-chlorobenzyl)-2,3-dibromo-5,5-dimethylcyclohexan-1-one 10 g (40.2 mmol) of the 2-(4-chlorobenzyl)-5,5-dimethylcyclohex-2-en-1-one obtained in (d) were dissolved in 50 ml 30/40 petroleum at 0° C. 6.72 g (40.2 mmol) bromine were then added to the solution. After 5-10 minutes, the solution decolourised and a precipitate formed. The solution was then cooled further and the precipitate filtered off to give 12.4 g 2-(4-chlorobenzyl)-2,3-dibromo-5,5-dimethylcyclohexan-1-one as a solid, m.pt. 82-84° C. Yield: 75 %.

(f) Preparation of 1-(4-chlorobenzyl)-3,3-dimethyl2-methoxycarbonylcyclopent-1-ene A solution of sodium methoxide was prepared by adding 2.8 g (121 mmol) sodium to 50 ml methanol. A slurry of the 2-(4-chlorobenzyl)-2,3-dibromo-5,5-dimethylcyclohexan-1-one obtained in (e) in methanol was then prepared and added to the sodium methoxide solution at reflux. Reflux was continued overnight. The reaction mixture was then quenched with 200 ml water, extracted twice with 100 ml aliquots of diethyl ether, backwashed with water, dried over anhydrous magnesium sulphate and flashed to give 8 g of a yellow oil. By gas chromatography anaylysis, it was established that 6.6 g 1-(4-chlorobenzyl)-3,3-dimethyl-2-methoxycarbonyl-cyclopent-1-ene were produced as an oil. The structure of the product was established by n.m.r. spectroscopy Yield: 78%.

(g) Preparation of 1-(4-chlorobenzyl)-1,2-epoxy-3,3-dimethyl-2-methoxycarbonylcyclopentane 23.5 g (3 equivalents) "PROXITANE 4002" (Trade Mark: 36-40% (w/w) peracetic acid in acetic acid) were added to 9.8 g (35.1 mmol) 1-(4-chlorobenzyl)-3,3-dimethyl-2-methoxycarbonylcyclopent-1-ene prepared as described in (f) in 90 ml trichloromethane The resulting mixture was refluxed for 3 hours, diluted with water and then the aqueous phase was re-extracted twice with 50 ml aliquots of trichloromethane, and the combined extracts backwashed once with 50 ml dilute sodium bicarbonate solution and twice with 50 ml aliquots of saturated sodium metabisulphite, washed with saturated sodium chloride solution, dried over anhydrous magnesium sulphate and flashed to give 12 g of a pale yellow oil which crystallised on cooling. Trituration in 30/40 petroleum gave 5.8 g 1-(4-chloro-benzyl)-1,2-epoxy3,3-dimethyl-2-methoxycarbonylcyclopentane as a white crystalline solid, m.pt. 86-87° C. Yield: 56%.

I claim:
1. A compound of the formula:

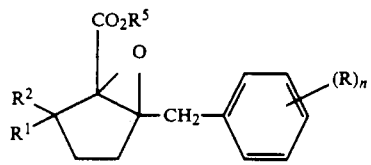

in which n represents an integer from 0 to 5;
each R represents a halogen atom, nitro, cyano, hydroxyl, $C_{1-12}$ alkyl, $C_{1-12}$ haloalkyl, $C_{1-12}$ alkoxy, $C_{1-12}$ haloalkoxy, amino, $C_{1-12}$ alkylamino, di- $C_{1-12}$ alkylamino, $C_{1-12}$ alkoxycarbonyl, carboxyl, $C_{1-12}$ alkanoyl, $C_{1-12}$ alkylthio, $C_{1-12}$ alkylsulphinyl, $C_{1-12}$ alkylsulphonyl, carbamoyl, $C_{1-12}$ alkylamindo, $C_{3-8}$ cycloalkyl or phenyl group; $R^1$ and $R^2$ independently represent a hydrogen atom or a $C_{1-12}$ alkyl group; and $R^5$ represents a hydrogen atom or a $C_{1-12}$ alkyl or $C_{3-8}$ cycloalkyl group.

2. A compound according to claim 1 in which $R^1$ and $R^2$ independently represent a hydrogen atom or a $C_{1-4}$alkyl group.

3. A compound according to claim 1 in which $R^1$ and $R^2$ independently represent a hydrogen atom or a methyl group.

4. A compound according to claim 1 in which R represents a halogen atom.

5. A compound according to claim 1 in which $R^5$ represents a hydrogen atom or a $C_{1-6}$alkyl group.

6. A compound according to claim 1 in which n is 1, R represents a chlorine atom, $R^1$ and $R^2$ both represent a hydrogen atom or both represent a methyl group and $R^5$ represents a methyl group.

7. A fungicidal composition which comprises a carrier and, as active ingredient, a compound of formula I as defined in claim 1.

8. A method of combating fungus at a locus which comprises treating the locus with a compound of formula I as defined in claim 1.

9. A method of combating fungus at a locus which comprises treating the locus with the composition of claim 8.

* * * * *

UNITED STATES PATENT AND TRADEMARK OFFICE
CERTIFICATE OF CORRECTION

PATENT NO. : 5,006,552
DATED : April 9, 1991
INVENTOR(S) : PAUL H. BRINER

It is certified that error appears in the above-identified patent and that said Letters Patent is hereby corrected as shown below:

Claim 1, column 11, lines 3 and 4, "$C_{1-12}$ alkylamindo" should read --$C_{1-12}$ alkylamido--.

Col. 12
Claim 9, line 3 of the claim, "8" should read --7--.

Signed and Sealed this

First Day of December, 1992

Attest:

DOUGLAS B. COMER

*Attesting Officer*  *Acting Commissioner of Patents and Trademarks*